United States Patent
Hu

(12) 
(10) Patent No.: US 6,413,362 B1
(45) Date of Patent: Jul. 2, 2002

(54) METHOD OF STEAM TREATING LOW YIELD PAPERMAKING FIBERS TO PRODUCE A PERMANENT CURL

(75) Inventor: Sheng-Hsin Hu, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/448,162

(22) Filed: Nov. 24, 1999

(51) Int. Cl.[7] .............................. D21B 1/32; D21B 1/36; D21C 5/02
(52) U.S. Cl. ................................ 162/4; 162/9; 162/21; 162/28; 162/68
(58) Field of Search .............................. 162/9, 68, 23, 162/24, 28, 4, 20, 21, 247

(56) References Cited

U.S. PATENT DOCUMENTS

| | | |
|---|---|---|
| 1,578,609 A | 3/1926 | Mason |
| 1,586,159 A | 5/1926 | Mason |
| 1,655,618 A | 1/1928 | Mason |
| 1,793,711 A | 2/1931 | Mitscherling |
| 1,824,221 A | 9/1931 | Mason |
| 1,872,996 A | 8/1932 | Mason |
| 1,906,885 A | 5/1933 | Richter |
| 1,922,313 A | 8/1933 | Mason |
| 1,979,341 A | 11/1934 | Olsen |
| 1,996,797 A | 4/1935 | Dreyfus |
| 2,234,188 A | 3/1941 | Morgan et al. |
| 2,516,847 A | 8/1950 | Boehm |
| 2,517,577 A | 8/1950 | Klug et al. |
| 2,524,024 A | 9/1950 | Swinehart et al. |
| 2,539,990 A | 1/1951 | Chapman et al. |
| 2,539,991 A | 1/1951 | Chapman |
| 2,583,994 A | 1/1952 | Shelton |
| 2,636,879 A | 4/1953 | Branan et al. |
| 2,639,281 A | 5/1953 | Hodge et al. |
| 2,645,577 A | 7/1953 | Bate et al. |
| 2,711,369 A | 6/1955 | Birdseye et al. |
| 2,878,118 A | 3/1959 | Rogers et al. |
| 2,882,965 A | 4/1959 | Wayman et al. |
| 2,904,460 A | 9/1959 | Nolan |
| 2,961,041 A | 11/1960 | Lesniak |
| 2,976,278 A | 3/1961 | Paddison et al. |

(List continued on next page.)

FOREIGN PATENT DOCUMENTS

| | | |
|---|---|---|
| CA | 798208 | 11/1968 |
| CA | 919468 | 1/1973 |
| CA | 1070537 | 1/1980 |
| CA | 1070646 | 1/1980 |
| CA | 1119033 | 3/1982 |
| CA | 1138708 | 1/1983 |
| CA | 1170487 | 7/1984 |

(List continued on next page.)

OTHER PUBLICATIONS

American Society for Testing Materials (ASTM) Designation: D 588–42, "Alpha–, Beta–, and Gamma–Cellulose in Paper," pp. 286–291, published as tentative from 1940 to 1942.

TAPPI Official Test Method T 200 om–89, "Laboratory Processing of Pulp (Beater Method)," published by the TAPPI Press, Atlanta, Georgia, revised 1989, pp. 1–5.

(List continued on next page.)

Primary Examiner—Steve Alvo
(74) Attorney, Agent, or Firm—Gregory E. Croft

(57) ABSTRACT

Wood fiber morphology can be permanently altered by introducing a substantial kink, twist, curl, crimp or other curvilinear deformation into a wood fiber. Wood fibers are first Fiberized using mechanical treatment processes and then are subjected to super atmospheric temperature/pressure steam explosion processing. The fiber morphology becomes a permanent characteristic of the fiber which is not relaxed in time, by contact with other treatments or through use.

16 Claims, 2 Drawing Sheets

U.S. PATENT DOCUMENTS

| | | |
|---|---|---|
| 2,999,783 A | 9/1961 | Terai et al. |
| 3,085,087 A | 4/1963 | Henry et al. |
| 3,251,824 A | 5/1966 | Battista |
| 3,347,855 A | 10/1967 | Nelson |
| 3,544,422 A | 12/1970 | Huff et al. |
| 3,567,573 A | 3/1971 | Case |
| 3,617,433 A | 11/1971 | Sutherland |
| 3,632,469 A | 1/1972 | Wilder |
| 3,652,387 A | 3/1972 | Wilder |
| 3,707,436 A | 12/1972 | O'Connor |
| 4,091,205 A | 5/1978 | Onda et al. |
| 4,163,687 A | 8/1979 | Mamers et al. |
| 4,250,305 A | 2/1981 | Saito et al. |
| 4,361,463 A | 11/1982 | Lindberg et al. |
| 4,401,813 A | 8/1983 | Lowell et al. |
| 4,431,479 A * | 2/1984 | Barbe et al. ............ 162/9 |
| 4,488,932 A | 12/1984 | Eber et al. |
| 4,645,541 A | 2/1987 | DeLong |
| 4,668,340 A | 5/1987 | Sherman |
| 4,710,187 A | 12/1987 | Boland et al. |
| 4,762,521 A | 8/1988 | Roessler et al. |
| 4,770,656 A | 9/1988 | Proxmire et al. |
| 4,798,603 A | 1/1989 | Meyer et al. |
| 4,798,651 A | 1/1989 | Kokta |
| 4,898,642 A | 2/1990 | Moore et al. |
| 4,971,658 A | 11/1990 | Henricson et al. |
| 4,995,943 A | 2/1991 | Rehberg |
| 5,021,122 A | 6/1991 | Desrochers et al. |
| 5,102,501 A | 4/1992 | Eber et al. |
| 5,122,228 A | 6/1992 | Bouchette et al. |
| 5,135,612 A | 8/1992 | Desrochers et al. |
| 5,247,072 A | 9/1993 | Ning et al. |
| 5,262,003 A | 11/1993 | Chupka et al. |
| 5,262,004 A | 11/1993 | Gilbert et al. |
| 5,382,610 A | 1/1995 | Harada et al. |
| 5,550,189 A | 8/1996 | Qin et al. |
| 5,843,852 A | 12/1998 | Dutkiewicz et al. |

FOREIGN PATENT DOCUMENTS

| | | |
|---|---|---|
| DE | 0 044 471 | 9/1887 |
| DE | 0 492 795 | 1/1926 |
| DE | 0 559 405 | 9/1927 |
| DE | 0 714 937 | 11/1941 |
| DE | 0 935 502 | 10/1955 |
| DE | 0 969 167 | 4/1958 |
| DE | 1 047 413 | 12/1958 |
| DE | 1 051 624 | 2/1959 |
| DE | 1 105 702 | 4/1961 |
| DE | 4 316 861 A1 | 11/1994 |
| EP | 0 038 373 A1 | 10/1981 |
| EP | 0 153 182 A2 | 8/1985 |
| EP | 0 172 135 A1 | 2/1986 |
| EP | 0 284 585 A2 | 9/1988 |
| EP | 0 346 559 A2 | 9/1989 |
| EP | 0 403 068 A2 | 12/1990 |
| EP | 0 501 059 A1 | 9/1992 |
| EP | 0 434 851 B1 | 8/1994 |
| EP | 0 446 556 B1 | 8/1995 |
| EP | 0 487 793 B1 | 8/1995 |
| FR | 1 000 674 | 2/1952 |
| FR | 1 026 696 | 4/1953 |
| FR | 2 544 222 | 10/1984 |
| GB | 0 374 047 | 5/1932 |
| GB | 0 945 127 | 12/1963 |
| GB | 2 000 822 A | 1/1979 |
| GB | 1 547 550 | 6/1979 |
| WO | WO 87/01402 A1 | 3/1987 |
| WO | WO 92/10606 A1 | 6/1992 |
| WO | WO 94/12719 A1 | 6/1994 |
| WO | WO 95/20065 A1 | 7/1995 |
| WO | WO 97/04162 A3 | 2/1997 |
| WO | WO 98/27269 A1 | 6/1998 |

OTHER PUBLICATIONS

TAPPI Official Test Method T 220 om–88, "Physical Testing of Pulp Handsheets," published by the TAPPI Press, Atlanta, Georgia, revised 1988, pp. 1–4.

TAPPI Offical Test Method T 203 om–88, "Alpha–, Beta–, and Gamma–Cellulose in Pulp," published by the TAPPI Press, Atlanta, Georgia, revised 1988, correction 1992, pp. 1–3.

TAPPI Official Test Method T 227 om–92, "Freeness of Pulp," published by the TAPPI Press, Atlanta, Georgia, revised 1992, pp. 1–7.

TAPPI Official Test Method T 227 om–92, "Freeness of Pulp," published by the TAPPI Press, Atlanta, Georgia, revised 1992, pp. 1–7.

TAPPI Official Test Method T 230 om–89, "Viscosity of Pulp (Capillary Viscometer Method)," published by the TAPPI Press, Atlanta, Georgia, revised 1989, pp. 1–6.

TAPPI Historical Method T 236 hm–85, "Kappa Number of Pulp," published by the TAPPI Press, Atlanta, Georgia, revised 1985, pp. 1–3.

TAPPI Classical Method T 254 cm–85, "Cupriethylenediamine Disperse Viscosity of Pulp (Falling Ball Method)," published by the TAPPI Press, Atlanta, Georgia, correction 1990, pp. 1–7.

Casey, J.P., "Pulp and Paper; Chemistry and Chemical Technology, 3rd edition, vol. I," John Wiley & sons, New York, 1980, pp. 25, 25, 411–421.

Karaivanova, S. et al., Paperchem Abstract AB3907662, "Preparation of Carboxymethylcellulose For The Textile Industry From Beechwood Prehydrolysis Kraft Pulp," *Khim. Ind.*(Sofia) 37, No. 2, 1965, pp. 49–54.

Naterova, A. et al., Paperchem Abstract AB4408005, "Conditions For The Preparation Of Carboxymethylcellulose— (1) Effect of the Agent Dose and Reaction Time," *Vyskum. Pr. Odboru Papiera Celulozy*, 18: V49–53 (1973).

Owczarzak, J., Paperchem Abstract AB6304383, "Properties of Beechwood (Fagus) Dissolving Pulp Manufactured With Acid–Steam Prehydrolysis," *Przegl. Papier*, 47, No. 10: 353–355, Oct. 1991).

Rydholm, Sven A., "Pulping Processes," Interscience Publishers, 1965, pp. 588, 618.

* cited by examiner

METHOD OF STEAM TREATING LOW YIELD PAPERMAKING FIBERS TO PRODUCE A PERMANENT CURL

FIELD OF THE INVENTION

The invention relates generally to fibrous materials and more specifically to fibrous materials made from wood products. The invention further relates to a blend of materials composed of Fiberized fibers and refined fibers exhibiting both high bulk and high strength. The invention further relates to processes that permanently change fiber morphology of a Fiberized wood fiber resulting in unchanging high bulk, maximized surface area, low density wood fiber products. Such properties arise from the permanent nature of the kink, twist, curl, crimp or other curvilinear deformations formed into the fiber. The blended fibers of the invention can be used in tissue, distribution layers, filter papers, and other applications where high bulk, high surface area, low density arising from the fiber morphology can be beneficially used.

BACKGROUND OF THE INVENTION

The use of steam or explosive decompression to disintegrate wood fibers is well-known in the art. For example, Mason discloses the general techniques of steam explosion treatments in Mason's U.S. Pat. Nos. 1,586,159; 1,578,609; 1,655,618; 1,824,221; 1,872,996; and 1,922,313. All of these patents are directed generally to the disintegration of primary cellulosic materials such as wood chips.

Later patents disclose incremental improvements and refinements in steam explosion treatments. For example, U.S. Pat. No. 2,516,847 to Boehm is directed to a means of sizing the exploded fibers. Mitscherling, U.S. Pat. No. 1,793,711, teaches use of a vacuum source to remove volatile resins prior to the pressurization and explosive decompression treatment by adding a series of explosive steps. Apparently this serves to more evenly disintegrate the fibers. This series of explosive steps permits the use of lower pressures and temperatures.

Mamers, et al., U.S. Pat. No. 4,163,687, is directed to a uniquely designed nozzle for assisting the liberation of fibers from cellulosic material during explosive defibration. The nozzle has a plurality of internal bars which form a tortuous path through which material must pass. O'Connor, U.S. Pat. No. 3,707,436, discloses using ammonia instead of steam. Apparently compounds such as ammonia are effective at swelling and plasticizing wood. Morgan, U.S. Pat. No. 2,234,188, is directed to production of light-colored cellulosic fiber. This is accomplished by first treating the chips or other small pieces of wood with an alkaline sulphite of alkaline metal such as sodium sulphite or potassium sulphite.

U.S. Pat. No. 4,488,932, to Robert J. Eber et al. discloses improved bulk and softness produced by using fiberized fibers. However, the curls and kinks relax significantly during the wet-forming process. As a result, the patent described the foam-forming process to make tissue. The fiberized fibers are dispersed in an aqueous foam which minimizes water absorption and, consequently, the reversal of the treated fibers to their original form.

U.S. Pat. No. 5,102,501, also to Robert J. Eber et al. discloses improving bulk and softness by depositing the fiberized fibers on the forming wire and dewatered in a period of time sufficiently shorter so that the fiberized fibers preserve their bulk-enhancing characteristics.

However, while past efforts have resulted in methods of controlling size, absorbance, and bulking characteristics, there is little, if any, teaching on methods useful in enhancing and preserving the curl and kink characteristics of the fiberized fibers. In addition, nothing in the past suggests that blending the fiberized/steam exploded fibers with highly refined fibers will form a sheet with higher bulk without losing strength.

Therefore, a need remains for a material which exhibits high bulk while retaining high strength.

SUMMARY OF THE INVENTION

In accordance with a first aspect of the invention there is provided a process for the production of a fiber having a permanently modified fiber morphology. The process includes:

(a) subjecting a papermaking fiber to mechanical deformation without substantial fiber breakage resulting in the fiber having a transient fiber morphology having a curl index of at least 0.15;

(b) subjecting the fiber with the transient fiber morphology to a treatment with steam at super atmospheric temperature and pressure for a sufficient period of time to render the fiber morphology permanent; and (c) explosively releasing the super atmospheric steam pressure.

The fiber resulting from this process has a permanent curl index of at least 0.2.

Another aspect of the invention is a process for the production of a fiber having a permanently modified fiber morphology. The process includes:

(a) subjecting a papermaking fiber to hammermilling without substantial fiber breakage resulting in a fiber with a curvilinear structure having a curl index of at least 0.2;

(b) subjecting the fiber with the curvilinear structure to treatment with steam at super atmospheric temperature and pressure for about 0.5 minutes to about 20 minutes, thus rendering the fiber morphology permanent; and (c) explosively releasing the super atmospheric steam pressure.

The fiber resulting from this process has a permanent curl index of at least 0.2.

Another aspect of the invention is an improved fiber material having increased bulk, which includes a blend of fibers having a permanent fiber morphology with a curl index of at least 0.2. This modified fiber is the product of the process of first mechanically deforming a papermaking wood fiber and subjecting the resulting fiber to steam at super atmospheric temperature and pressure to obtain the permanent fiber morphology. This modified fiber is blended with a refined papermaking wood fiber. There is about 0.01 to about 100 parts of the fiber having a permanent fiber morphology per each one part by weight of the refined papermaking fiber. This improved fiber material has a bulk greater than 3.0 cm$^3$/g.

The fiber material can form sheets with high bulk and high strength. This fiber material could be used in tissue, towel or saturation paper basesheets. In addition, this material could be used as wicking distribution material. The invention is further directed to a fiber material which is created from a blend of Fiberized and refined fibers.

DETAILED DESCRIPTION

Figure 1:
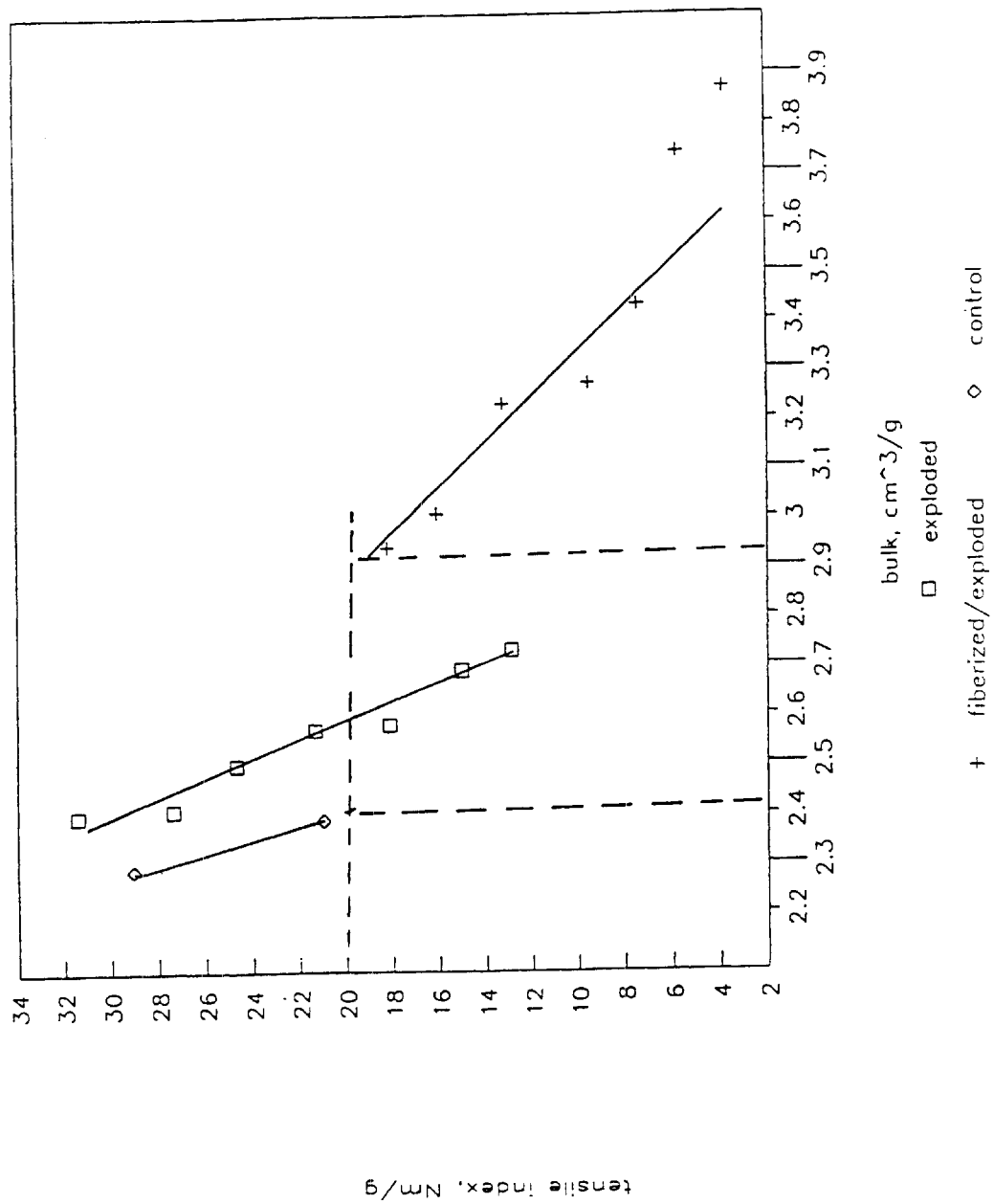
FIG. 1 is a graph of tensile index verses bulk. Three lines are charted on the graph. One line is the control (untreated) data. Another line is the steam exploded data. A final line is the Fiberized/steam explosion data.
Figure 2:
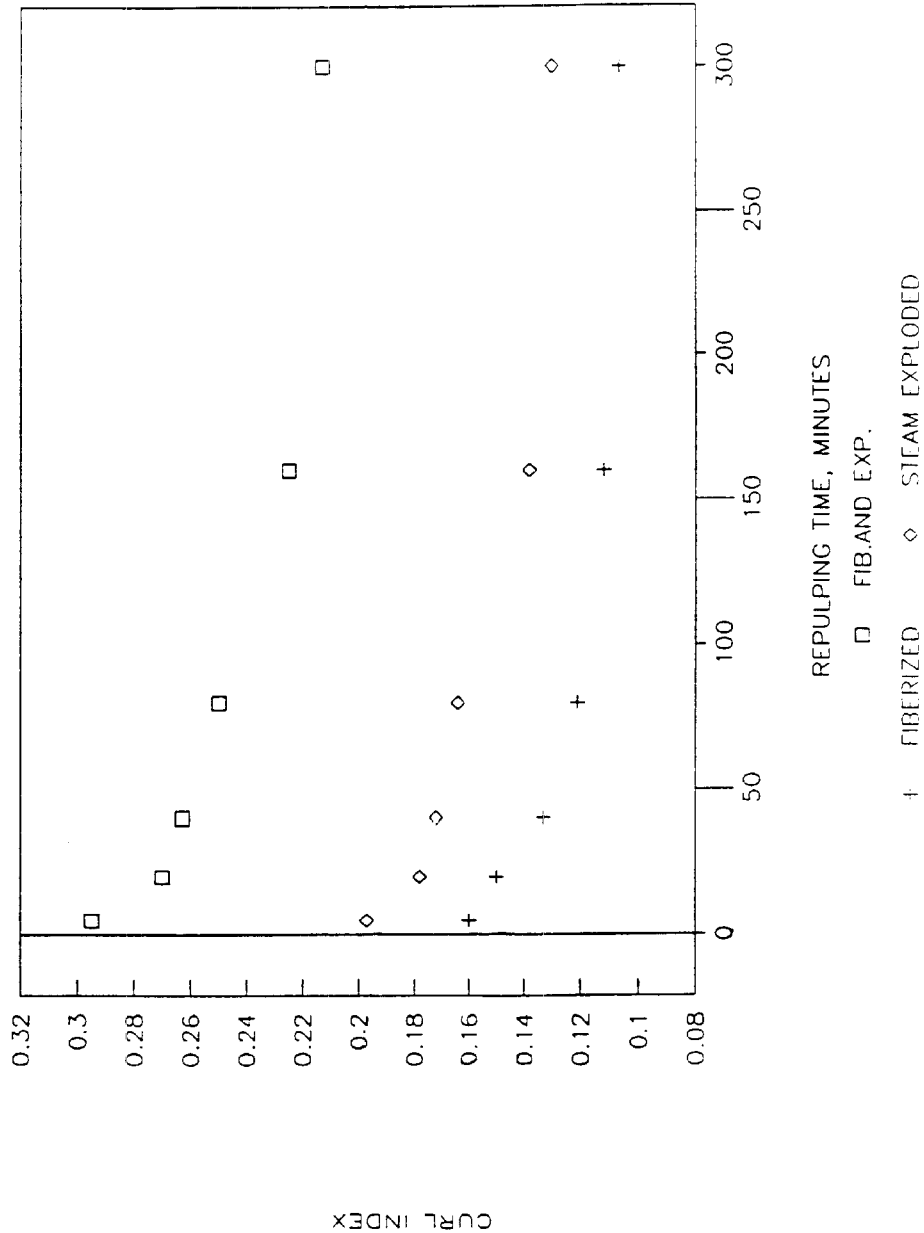
FIG. 2 is titled curl performance and graphs curl index verses repulping time. Three sets of data is charted on the graph. One set is the Fiberized data. One set is the steam exploded data. A final set is Fiberized/steam exploded data.

A process for the production of a fiber having a permanently modified fiber morphology. The process includes:

(a) subjecting a papermaking fiber to mechanical deformation without substantial fiber breakage resulting in the fiber having a transient fiber morphology having a curl index of at least 0.15;

(b) subjecting the fiber with the transient fiber morphology to a treatment with steam at super atmospheric temperature and pressure for a sufficient period of time to render the fiber morphology permanent; and (c) explosively releasing the super atmospheric steam pressure. The fiber resulting from this process has a permanent curl index of at least 0.2.

It has been discovered that by using a mechanical deformation and steam explosion process for treating cellulosic fibers, at the appropriate treatment conditions, modified cellulosic fibers exhibiting desired properties may be prepared by an efficient and effective process.

A wide variety of cellulosic fibers can be employed in the process of the invention. Illustrative cellulosic fibers include, but are not limited to, wood and wood products, such as wood pulp fibers; non-woody paper-making fibers from cotton, from straws and grasses, such as rice and esparto, from canes and reeds, such as bagasse, from bamboos, from stalks with bast fibers, such as jute, flax, kenaf, cannabis, linen and ramie, and from leaf fibers, such as abaca and sisal. It is also possible to use mixtures of one or more cellulosic fibers. Suitably, the cellulosic fiber used is from a wood source. Suitable wood sources include softwood sources such as pines, spruces, and firs, and hardwood sources such as oaks, eucalyptuses, poplars, beeches, and aspens.

As used herein, the term "fiber" or "fibrous" is meant to refer to a particulate material wherein the length to diameter ratio of such particulate material is greater than about 10. Conversely, a "nonfiber" or "nonfibrous" material is meant to refer to a particulate material wherein the length to diameter ratio of such particulate material is about 10 or less or more nearly 2 or less.

In the invention, it is desired that the cellulosic fibers be used in a form wherein the cellulosic fibers have already been refined into a pulp. As such, the cellulosic fibers will be substantially in the form of individual cellulosic fibers although such individual cellulosic fibers may be in an aggregate form such as a pulp sheet. The current process, then, is in contrast to known steam explosion processes that generally treat cellulosic fibers that are typically in the form of virgin wood chips or the like. Thus, the current process is a post-pulping, cellulosic fiber modifying process as compared to known steam explosion processes that are generally used for high-yield pulp manufacturing or waste-recycle processes.

The cellulosic fibers used in the steam explosion process are desirably low yield cellulosic fibers. As used herein, "low yield" cellulosic fibers are those cellulosic fibers produced by pulping processes beneficially providing a yield of about 85 percent or less, suitably of about 80 percent or less, and more suitably of about 55 percent or less. In contrast, "high yield" cellulosic fibers are those cellulosic fibers produced by pulping processes beneficially providing a yield of about 85 percent or greater. Such pulping processes generally leave the resulting cellulosic fibers with high levels of lignin.

As used herein, the term "permanent fiber morphology" is defined as a fiber characteristic which remains after the fiber has been repulped for up to 300 minutes and preferrably between 150 and 300 minutes. The term "transient or temporary fiber morphology" is defined as a fiber characteristic which does not remain after the fiber has been repulped for up to 150 minutes.

In the process of the invention, it has been discovered that the use of mechanical deformation followed by steam explosion produced fibers which displayed permanent curl morphology. This permanent change in fiber morphology has a positive effect on the specific volume (bulk) and absorbent properties of sheets made from such fibers. This fiber curl morphology becomes a permanent characteristic of the fiber which is not relaxed in time, by contact with other treatments or through use.

The fibers can be mechanically deformed to achieve a temporary curl morphology. This mechanical deformation should not cause substantial fiber breakage. Various refining and hammermilling methods known in the art can be used to provide temporary curl morphology. The preferred means for mechanically deforming the fiber is the hammermill.

In general the fiber enters the hammermill with an equilibrium moisture content of 15% by weight. The fiber exists the hammermill with an equilibrium moisture content of 1–5% by weight. The hammermill operates at a temperature range usually between 50° C. to 100° C.

The temporary curl morphology created by the hammermill is primarily caused by shearing forces upon the fibers as they pass between the anvil and the rotating hammer. The average residence time of the fibers in the hammermill is generally less than a second. Following mechanical deformation the fiber displays a curl index that is generally greater than 0.15 and usually greater than 0.2. The fiber's temporary curl morphology is enhanced and made permanent by the subsequent steam explosion treatment.

Following mechanical deformation, the fibers are subjected to a steam explosion treatment. Also, the use of steam explosion alone can be sufficient to effectively modify cellulosic fibers such that the modified cellulosic fibers exhibit desired properties, particularly desired liquid absorbency properties. In general, it is desired that the cellulosic fibers are cooked in a saturated steam environment that is substantially free of air. The presence of air in the pressurized cooking environment may result in the oxidation of the cellulosic fibers. As such, it is desired that the cellulosic fibers are cooked in a saturated steam environment that beneficially comprises less than about 5 weight percent, suitably less than about 3 weight percent, and more suitably less than about 1 weight percent of air, based on the total weight of the gaseous environment present in the pressurized cooking environment.

The individual cellulosic fibers are steam cooked at a high temperature and at a high pressure. In general, any combination of high pressure, high temperature, and time which is effective in achieving a desired degree of modification, without undesirable damage to the cellulosic fibers, so that the cellulosic fibers exhibit the desired fiber curl properties as described herein, is suitable for use in the invention.

Generally, if the temperature used is too low, there will not be a substantial and/or effective amount of modification of the cellulosic fibers that occurs. Also, generally, if the temperature used is too high, a substantial degradation of the cellulosic fibers may occur which will negatively affect the properties exhibited by the treated cellulosic fibers. As such, as a general rule, the cellulosic fibers will be treated at a temperature within the range beneficially from about 130° C. to about 250° C., suitably from about 150° C. to about 225° C., more suitably from about 160° C. to about 225° C., and most suitably from about 160° C. to about 200° C.

Generally, the cellulosic fibers will be subjected to an elevated superatmospheric pressure over a time period within the range of from about 0.1 minute to about 30 minutes, beneficially from about 0.5 minute to about 20 minutes, and suitably from about 1 minute to about 10 minutes. In general, the higher the temperature employed, the shorter the period of time generally necessary to achieve a desired degree of modification of the cellulosic fibers. As such, it may be possible to achieve essentially equivalent amounts of modification for different cellulosic fiber samples by using different combinations of high temperatures and times.

Generally, if the pressure used is too low, there will not be a substantial and/or effective amount of modification of the cellulosic fibers that occurs. Also, generally, if the pressure used is too high, a substantial degradation of the cellulosic fibers may occur which will negatively affect the properties exhibited by the crosslinked cellulosic fibers. As such, as a general rule, the cellulosic fibers will be treated at a pressure that is superatmospheric (i.e. above normal atmospheric pressure), beneficially within the range from about 40 to about 405 pounds per square inch, suitably from about 40 to about 230 pounds per square inch, and more suitably from about 90 to about 230 pounds per square inch.

As used herein, "consistency" is meant to refer to the concentration of the cellulosic fibers present in an aqueous mixture. As such, the consistency will be presented as a weight percent representing the weight amount of the cellulosic fibers present in an aqueous mixture divided by the total weight amount of cellulosic fibers and water present in such mixture, multiplied by 100.

In general, the cellulosic fibers may be used in the process of the invention in either a dry or a wet state. However, it may be desirable to prepare an aqueous mixture comprising the cellulosic fibers wherein the aqueous mixture is agitated, stirred, or blended to effectively disperse the cellulosic fibers throughout the water. In one embodiment of the invention, it is desired that the cellulosic fibers be steam cooked when the cellulosic fibers are in the form of aqueous pulp mixture that beneficially has a consistency of between about 10 to about 100 weight percent, suitably between about 20 to about 80 weight percent, and more suitably between about 25 to about 75 weight percent cellulosic fibers, based on the total weight percent of the aqueous pulp mixture.

The cellulosic fibers are typically mixed with an aqueous solution beneficially comprising at least about 30 weight percent water, suitably about 50 weight percent water, more suitably about 75 weight percent water, and most suitably 100 weight percent water. When another liquid is employed with the water, such other suitable liquids include methanol, ethanol, isopropanol, and acetone. However, the use or presence of such other non-aqueous liquids may impede the formation of an essentially homogeneous mixture such that the cellulosic fibers do not effectively disperse into the aqueous solution and effectively or uniformly mix with the water. Such a mixture should generally be prepared under conditions that are sufficient for the cellulosic fibers and water to be effectively mixed together. Generally, such conditions will include using a temperature that is between about 10° C. to about 100° C.

In general, cellulosic fibers are prepared by pulping or other preparation processes in which the cellulosic fibers are present in an aqueous solution. For use in the steam explosion treatment of the invention, therefore, it may be possible to use an aqueous solution directly from such preparation processes without having to separately recover the cellulosic fibers.

After steam cooking the cellulosic fibers, the pressure is released and the cellulosic fibers are exploded into a release vessel. The pressure may be released by venting or released by various methods known in the art.

The equipment or method used to treat the cellulosic fibers with steam explosion is generally not critical. Suitable equipment and methods for steam explosion may be found, for example, in Canadian Patents No. 1,070,537, dated Jan. 29, 1980; Canadian Patent No. 1,070,646, dated Jan. 29, 1980; Canadian Patent No. 1119,033, dated Mar. 2, 1982; Canadian Patent No. 1,138,708, dated Jan. 4, 1983; and U.S Patent No. 5,262,003, issued Nov. 16, 1993, all of which are incorporated herein in their entirety by reference.

The steam explosion process generally causes the cellulosic fibers to become modified. Without intending to be bound hereby, it is believed that the mechanical deformation/steam explosion process causes the cellulosic fibers to undergo a curling phenomenon. The steam exploded cellulosic fibers, in addition to being modified, have been discovered to exhibit improved properties that make such steam exploded cellulosic fibers suitable for use in liquid absorption or liquid handling applications.

Cellulosic fibers suitable for use in the invention are generally without a substantial amount of curl prior to the mechanical deformation/steam explosion process (generally less than 0.2 curl index). After such mechanical deformation/steam explosion process, the treated cellulosic fibers will generally exhibit a desired level of stable curl (generally greater than 0.2 curl index). As such, the process of the invention generally does not require the use of any additional additives to the cellulosic fibers during the steam explosion process or any post-treatment steps after the steam explosion of the fibers to achieve the desired curls.

In one embodiment of the invention, the cellulosic fibers will be considered to be effectively treated by the steam explosion process when the cellulosic fibers exhibit an effective Wet Curl value of greater than 0.2.

The curl of a fiber may be quantified by a curl value which measures the fractional shortening of a fiber due to kink, twists, and/or bends in the fiber. For the purposes of this invention, a fiber's curl value is measured in terms of a two dimensional plane, determined by viewing the fiber in a two dimensional plane. To determine the curl value of a fiber, the projected length of a fiber as the longest dimension of a two dimensional rectangle encompassing the fiber, I, and the actual length of the fiber, L, are both measured. An image analysis method may be used to measure L and I. A suitable image analysis method is described in U.S. Pat. No. 4,898,642, incorporated herein in its entirety by reference. The curl value of a fiber can then be calculated from the following equation:

$$\text{Curl Value} = (L/I) - 1$$

Depending on the nature of the curl of a cellulosic fiber, such curl may be stable when the cellulosic fiber is dry but may be unstable when the cellulosic fiber is wet. The cellulosic fibers prepared according to the process of the invention have been found to exhibit a substantially stable fiber curl when wet. This property of the cellulosic fibers may be quantified by a Wet Curl value, as measured according to the test method described herein, which is a length weighted mean curl average of a designated number of fibers, such as about 4000, from a fiber sample. As such, the Wet Curl value is the summation of the individual wet curl values for each fiber multiplied by the fiber's actual length, L, divided by the summation of the actual lengths of the fibers. It is hereby noted that the Wet Curl value, as determined herein, is calculated by only using the necessary values for those fibers with a length of greater than about 0.4 millimeter.

As used herein, the cellulosic fibers will be considered to be effectively treated by the steam explosion treatment when the cellulosic fibers exhibit a Wet Curl value that is greater than about 0.2, beneficially between about 0.2 to about 0.4, more beneficially between about 0.2 to about 0.35, suitably between about 0.22 to about0.33, and suitably between about 0.25 to about 0.33. In contrast, cellulosic fibers that have not been treated generally exhibit a Wet Curl value that is less than about 0.2.

After the cellulosic fibers have been effectively mechanically deformed/steam exploded, the treated cellulosic fibers are suitable for use in a wide variety of applications. However, depending on the use intended for the treated cellulosic fibers, such treated cellulosic fibers may be washed with water. If any additional processing procedures are planned because of the specific use for which the treated cellulosic fibers are intended, other recovery and post-treatment steps are also well known.

New fiber materials can be produced by blending highly refined fibers with the mechanically deformed/steam exploded high bulk fibers. Highly refined fibers are raw fibers that are refined to a freeness of about 300–500 C.S.F. As shown in Table 2 and 3 and FIG. 1, at certain blend ratios, the blended fibers form a sheet with much higher bulk without losing strength, compared to the untreated fiber sheets.

The cellulosic fibers treated according to the process of the invention are suited for use in disposable absorbent products such as diapers, adult incontinent products, and bed pads; in catamenial devices such as sanitary napkins, and tampons; other absorbent products such as wipes, bibs, wound dressings, and surgical capes or drapes; and tissue-based products such as facial or bathroom tissues, household towels, wipes and related products. Accordingly, in another aspect, the invention relates to a disposable absorbent product comprising the cellulosic fibers treated according to the process of the invention.

In one embodiment of the invention, the treated fibers prepared according to the process of the invention are formed into a handsheet which might represent a tissue-based product. Such a handsheet may be formed by either a wet-laid or an air-laid process. A wet-laid handsheet may be prepared according to the method disclosed in the Test Methods section herein.

It has been discovered that a wet-laid handsheet prepared from the treated cellulosic fibers prepared according to the process of the invention may exhibit a density that is lower than a wet-laid handsheet prepared from cellulosic fibers that have not been treated according to the process of the invention.

It has also been discovered that a wet-laid handsheet prepared from the treated cellulosic fibers prepared according to the process of the invention may exhibit an increased bulk and higher absorbent capacity than a wet-laid handsheet prepared from cellulosic fibers that have not been treated according to the process of the invention.

In one embodiment of the invention, the treated cellulosic fibers prepared according to the process of the invention are formed into a fibrous matrix for incorporation into an absorbent structure. A fibrous matrix may take the form of, for example, a batt of comminuted wood pulp fluff, a tissue layer, a hydroentangled pulp sheet, or a mechanically softened pulp sheet. An exemplary absorbent structure is generally described in copending U.S. patent application Ser. No. 60/008,994, which reference is incorporated herein in its entirety by reference.

A fibrous matrix useful in the invention may be formed by an air-laying process or a wet-laid process, or by essentially any other process known to those skilled in the art for forming a fibrous matrix.

In one embodiment of the invention, a disposable absorbent product is provided, which disposable absorbent product comprises a liquid-permeable topsheet, a backsheet attached to the liquid-permeable topsheet, and an absorbent structure positioned between the liquid-permeable topsheet and the backsheet, wherein the absorbent structure comprises treated cellulosic fibers prepared using the process of the invention.

Exemplary disposable absorbent products are generally described in U.S. Pat. Nos. 4,710,187; 4,762,521; 4,770,656; and 4,798,603; which references are incorporated herein by reference.

Those skilled in the art will recognize materials suitable for use as the topsheet and backsheet. Exemplary of materials suitable for use as the topsheet are liquid-permeable materials, such as spunbonded polypropylene or polyethylene having a basis weight of from about 15 to about 25 grams per square meter. Exemplary of materials suitable for use as the backsheet are liquid-impervious materials, such as polyolefin films, as well as vapor-pervious materials, such as microporous polyolefin films.

Absorbent products and structures according to all aspects of the invention are generally subjected, during use, to multiple insults of a body liquid. Accordingly, the absorbent products and structures are desirably capable of absorbing multiple insults of body liquids in quantities to which the absorbent products and structures will be exposed during use. The insults are generally separated from one another by a period of time.

Test Procedures

Wet Curl

The Wet Curl value for fibers was determined by using an instrument which rapidly, accurately, and automatically determines the quality of fibers, the instrument being available from OpTest Equipment Inc., Hawkesbury, Ontario, Canada, under the designation Fiber Quality Analyzer, OpTest Product Code DA93.

A sample of dried cellulosic fibers was obtained. The cellulosic fiber sample was poured into a 600 milliliter plastic sample beaker to be used in the Fiber Quality Analyzer. The fiber sample in the beaker was diluted with tap water until the fiber concentration in the beaker was about 10 to about25 fibers per second for evaluation by the Fiber Quality Analyzer.

An empty plastic sample beaker was filled with tap water and placed in the Fiber Quality Analyzer test chamber. The <System Check> button of the Fiber Quality Analyzer was then pushed. If the plastic sample beaker filled with tap water was properly placed in the test chamber, the <OK> button of the Fiber Quality Analyzer was then pushed. The Fiber Quality Analyzer then performs a self-test. If a warning was not displayed on the screen after the self-test, the machine was ready to test the fiber sample.

The plastic sample beaker filled with tap water was removed from the test chamber and replaced with the fiber sample beaker. The <Measure> button of the Fiber Quality Analyzer was then pushed. The <New Measurement> button of the Fiber Quality Analyzer was then pushed. An identification of the fiber sample was then typed into the Fiber Quality Analyzer. The <OK> button of the Fiber Quality Analyzer was then pushed. The <Options> button of the Fiber Quality Analyzer was then pushed. The fiber count was set at 4,000. The parameters of scaling of a graph to be printed out may be set automatically or to desired values. The <Previous> button of the Fiber Quality Analyzer was then pushed. The <Start> button of the Fiber Quality Analyzer was then pushed. If the fiber sample beaker was properly placed in the test chamber, the <OK> button of the Fiber Quality Analyzer was then pushed. The Fiber Quality Analyzer then began testing and displayed the fibers passing through the flow cell. The Fiber Quality Analyzer also displayed the fiber frequency passing through the flow cell, which should be about 10 to about 25 fibers per second. If the fiber frequency is outside of this range, the <Stop> button of the Fiber Quality Analyzer should be pushed and the fiber sample should be diluted or have more fibers added to bring the fiber frequency within the desired range. If the fiber frequency is sufficient, the Fiber Quality Analyzer tests the fiber sample until it has reached a count of 4000 fibers at which time the Fiber Quality Analyzer automatically stops. The <Results> button of the Fiber Quality Analyzer was then pushed. The Fiber Quality Analyzer calculates the Wet Curl value of the fiber sample, which prints out by pushing the <Done> button of the Fiber Quality Analyzer.

Procedures for Refined Fiber Preparation

Refined fiber was prepared using a Laboratory Valley beater according to TAPPI (Technical Association of Pulp and Paper Industry) test method (T200 om-89). The C. S. Freeness of the fiber is the measurement of the degree of fiber refining and measured according to TAPPI (Technical Association of Pulp and Paper Industry test method (T227 om-92).

Preparation of Wet-Laid Handsheet

A) Handsheet Forming

A 7½ inch by 7½ inch handsheet having a basis weight of about 60 grams per square meter was prepared using a Valley Handsheet mold, 8×8 inches. The sheet mold forming wire is a 90×90 mesh, stainless-steel wire cloth, with a wire diameter of 0.0055 inch. The backing wire is a 14×14 mesh with a wire diameter of 0.021 inch, plain weave bronze. Taking a sufficient quantity of the thoroughly mixed stock to produce a handsheet of about 60 grams per square meter, the stock container of the sheet mold was clamped in position on the wire. Several inches of water was allowed to rise above the wire. The measured stock was added and the mold was filled with water up to a mark of 6 inches above the wire. The perforated mixing plate was inserted into the mixture in the mold and slowly moved down and up 7 times. The water leg drain valve was immediately opened. When the water and stock mixture drained down to and disappeared from the wire, the drain valve was closed. The cover of the sheet mold was raised. A clean, dry blotter was carefully placed on the formed fibers. The dry couch roll was placed at the front edge of the blotter. The fibers adhering to the blotter were couched off the wire by one passage of the couching roll, without pressure, from front to back of wire.

B) Handsheet Pressing

The blotter with the fiber mat adhering to it was placed in the hydraulic press, handsheet up, on top of two used, re-dried blotters. Two new blotters were placed on top of the handsheet. The press was closed and clamped. Pressure was applied to give a gauge reading that produced 75 PSI on the area of the blotter affected by the press. This pressure was maintained for exactly one minute. The pressure on the press was then released. The press was opened and the handsheet was removed.

C) Handsheet Drying

The handsheet was placed on the polished surface of the sheet dryer (Valley Steam hot plate). The canvas cover was carefully lowered over the sheet. The 13 lb dead weight was fastened to the lead filled brass tube. The sheet was allowed to dry for 2 minutes. The surface temperature, with the cover removed, averaged 100.5 plus or minus 1 degree C. The sheet was removed from the dryer and trimmed to 7½×7½ inches. The sheet was immediately weighed.

D) Testing of Handsheets

Handsheets were tested at 50% humidity and 73 degree F. Bulk, Burst Indes, Tear index and tensile index of the handsheets were tested according to TAPPI (Technical Association of Pulp and Paper Industry) test method (T220 om-88).

Bulk and Dry Density of an Absorbent Structure

From a handsheet prepared according to the procedure described herein, a strip of sample handsheet material, having a width of about 2 inches and a length of about 15 inches, was obtained by using a textile saw available, for example from Eastman, Machine Corp., Buffalo, N.Y. The sample strip was cut at least about 1 inch away from the edge of the handsheet so as to avoid edge effects. The sample strip was marked in about 10 millimeter intervals using water-soluble ink.

To measure the bulk of the sample strip, a bulk meter accurate to at least about 0.01 millimeter, such as a bulk meter available from Mitutoyo Corporation, was used. An about one inch diameter platen was used to measure the bulk, with the platen being parallel to the base of the bulk meter. The bulk of the sample strip was measured in about 50 millimeter intervals along the length of the sample strip and then averaged. The average bulk of the sample strip was then used to calculate the dry density of the sample strip, using the weight and dimensions of the sample strip. The wet density of the sample strip may be similarly determined after the sample strip has evaluated for Liquid Flux values.

Experimental Results

The basic raw material was Kimberly-Clark's northern softwood (i.e., LL19) kraft. The fibers were divided into two parts. One part of the raw fibers was Fiberized using a lab Pullmann fiberizer; then the Fiberized fibers were subjected to steam explosion treatment. These combined treatments can produce fibers which form very bulky but very weak sheets. The other part of the raw fibers was refined to a low freeness (about 300 ml C.S.F.) using a lab Valley beater. New fiber materials can be produced by blending the highly-refined fibers with the high bulk, weak fibers at various bonding ratios. At certain blend ratios, the blended fibers form a much higher bulk without losing strength compared to the untreated.

Table 1 shows the properties of fiber (LL-19) as it is refined from 0 to 60 minutes in a Valley Beater.

Table 2 shows the physical properties of various blends of 60 minute refined fiber (LL-19) and steam exploded fiber (LL-19).

Table 3 shows the physical properties of various blends of 60 minute refined fiber (LL-19) and Fiberized/steam exploded fiber (LL-19).

TABLE 1

Valley Beater Date LL-19

| MINUTES | | 0 | 3 | 5 | 15 | 30 | 45 | 60 |
|---|---|---|---|---|---|---|---|---|
| C.S. FREENESS | (ml) | 705 | 695 | 685 | 635 | 560 | 430 | 315 |
| BURST INDEX | (kPam^2/g) | 1.06 | 1.62 | 2.24 | 4.59 | 6.22 | 7.89 | 8.04 |
| BULK | (cm^3/g) | 2.39 | 2.29 | 2.15 | 1.99 | 1.84 | 1.81 | 1.68 |
| SCOTT BOND | (ft.lb.) | 0.022 | 0.030 | 0.038 | 0.150 | 0.225 | 0.388 | >.500 |
| TENSILE INDEX | (Nm/g) | 20.97 | 29.04 | 36.45 | 65.14 | 80.46 | 97.82 | 102.09 |
| STRETCH | (%) | 1.76 | 2.24 | 2.46 | 3.61 | 4.07 | 4.65 | 4.64 |
| T.E.A. | (J/m^2) | 13.47 | 24.66 | 33.71 | 84.60 | 114.21 | 150.50 | 156.49 |
| OPACITY, ISO | (%) | 76.8 | 76.6 | 74.9 | 73.5 | 70.4 | 69.9 | 67.7 |
| SCATTERING COEF. | (m^2/kg) | 37.55 | 37.32 | 34.14 | 31.63 | 27.03 | 26.34 | 23.67 |
| ABSORPTION COEF. | (sqm/kg) | 0.24 | 0.24 | 0.24 | 0.26 | 0.28 | 0.28 | 0.29 |
| POROSITY, Frazier | (cfm/ft^2) | 80.5 | 54.4 | 43.5 | 16.0 | 6.5 | 2.0 | 1.5 |

TABLE 2

| BLEND ID | A | B | C | D | E | F | G |
|---|---|---|---|---|---|---|---|
| LL-19 (Valley Beater Refined 60 Min) | 0 | 5% | 10% | 15% | 20% | 25% | 30% |
| LL-19 Exploded (2 Min/200 C/75% Cons) | 100% | 95% | 90% | 85% | 80% | 75% | 70% |
| PFI REVOLUTIONS | 0 | 0 | 0 | 0 | 0 | 0 | 0 |
| SI CONVERTED AVERAGE TEST DATA | | | | | | | |
| Burst Index (kPam^2/g) | 0.60 | 0.82 | 1.10 | 1.33 | 1.63 | 1.86 | 2.22 |
| Specific Volume (cm^3/g) | 2.73 | 2.69 | 2.58 | 2.57 | 2.50 | 2.41 | 2.40 |
| Tear Index (mNm^2/g) | 8.88 | 9.40 | 12.96 | 13.96 | 16.82 | 18.27 | 18.83 |
| Tensile Index (Nm/g) | 12.87 | 15.03 | 18.11 | 21.31 | 24.67 | 27.36 | 31.42 |
| Tensile Energy Absorp. (J/m^2) | 5.92 | 8.18 | 12.32 | 16.78 | 21.40 | 24.83 | 31.77 |
| AVERAGE PHYSICAL TEST DATA | | | | | | | |
| C.S. Freeness (ml) | 705 | 685 | 680 | 665 | 655 | 625 | 600 |
| Burst (psi) | 5.2 | 7.1 | 9.6 | 11.6 | 14.2 | 16.2 | 19.3 |
| Bulk (in) | 0.0064 | 0.0064 | 0.0061 | 0.0061 | 0.0059 | 0.0057 | 0.0057 |
| Tear (g) | 54.3 | 57.5 | 79.3 | 85.4 | 102.9 | 111.8 | 115.2 |
| Tensile (lbs) | 4.38 | 5.11 | 6.16 | 7.24 | 8.39 | 9.30 | 10.68 |
| Stretch (%) | 1.385 | 1.556 | 1.873 | 2.097 | 2.317 | 2.439 | 2.659 |
| Tensile Energy Absorp. (ftlb/ft^2) | 0.405 | 0.561 | 0.844 | 1.149 | 1.466 | 1.701 | 2.176 |
| Scott Internal Bond (ftlb) | 0.026 | 0.024 | 0.027 | 0.031 | 0.031 | 0.034 | 0.038 |
| Porosity (Frazier) (cfm/ft^2) | 128.4 | 94.1 | 89.3 | 66.3 | 62.0 | 55.1 | 35.6 |
| AVERAGE OPTICAL TEST DATA | | | | | | | |
| (ISO) Brightness (%) | 84.44 | 84.56 | 84.64 | 84.65 | 84.77 | 84.66 | 84.75 |
| (ISO) Opacity (%) | 78.57 | 78.23 | 78.26 | 77.65 | 78.02 | 77.78 | 77.48 |
| Scattering Coefficient (m^2/kg) | 40.22 | 39.65 | 39.81 | 38.67 | 39.40 | 38.82 | 38.29 |
| Absorption Coefficient (m^2/kg) | 0.28 | 0.28 | 0.27 | 0.27 | 0.27 | 0.27 | 0.27 |
| L* (%) | 95.52 | 95.53 | 95.57 | 95.54 | 95.57 | 95.51 | 95.50 |
| a* (%) | −0.19 | −0.18 | −0.20 | −0.20 | −0.20 | −0.20 | −0.20 |
| b* (%) | 3.38 | 3.29 | 3.26 | 3.20 | 3.15 | 3.12 | 3.03 |

TABLE 3

| BLEND ID | H | I | J | K | L | M | N |
|---|---|---|---|---|---|---|---|
| LL-19 (Valley Beater Refined 60 Min) | 0 | 5% | 10% | 15% | 20% | 25% | 30% |
| LL-19 Fiberized, Exploded (2 Min/200 C/75% Cons) | 100% | 95% | 90% | 85% | 80% | 75% | 70% |
| PFI REVOLUTIONS | 0 | 0 | 0 | 0 | 0 | 0 | 0 |
| SI CONVERTED AVERAGE TEST DATA | | | | | | | |
| Burst Index (kPam^2/g) | 0.15 | 0.24 | 0.40 | 0.60 | 0.79 | 1.00 | 1.29 |
| Specific Volume (cm^3/g) | 3.87 | 3.74 | 3.43 | 3.27 | 3.23 | 3.01 | 2.94 |
| Tear Index (mNm^2/g) | 4.64 | 6.08 | 7.20 | 9.48 | 11.62 | 12.37 | 13.44 |
| Tensile Index (Nm/g) | 3.74 | 5.72 | 7.37 | 9.50 | 13.22 | 16.07 | 18.19 |
| Tensile Energy Absorp. (J/m^2) | 0.85 | 1.57 | 2.54 | 3.99 | 8.21 | 11.31 | 11.96 |
| AVERAGE PHYSICAL TEST DATA | | | | | | | |
| C.S. Freeness (ml) | 735 | 730 | 720 | 710 | 700 | 660 | 670 |
| Burst (psi) | 1.3 | 2.1 | 3.5 | 5.2 | 6.9 | 8.7 | 11.2 |
| Bulk (in) | 0.0091 | 0.0088 | 0.0081 | 0.0077 | 0.0076 | 0.0071 | 0.0069 |
| Tear (g) | 28.4 | 37.2 | 44.1 | 58.0 | 71.1 | 75.7 | 82.2 |
| Tensile (lbs) | 1.27 | 1.94 | 2.51 | 3.23 | 4.49 | 5.46 | 6.18 |

TABLE 3-continued

| BLEND ID | H | I | J | K | L | M | N |
|---|---|---|---|---|---|---|---|
| Stretch (%) | 0.821 | 0.925 | 1.071 | 1.200 | 1.628 | 1.854 | 1.779 |
| Tensile Energy Absorp. (ftlb/ft^2) | 0.058 | 0.108 | 0.174 | 0.274 | 0.563 | 0.774 | 0.819 |
| Scott Internal Bond (ftlb) | 0.014 | 0.020 | 0.022 | 0.026 | 0.030 | 0.034 | 0.038 |
| Porosity (Frazier) (cfm/ft^2) | 422.7 | 304.5 | 283.4 | 203.0 | 188.6 | 165.4 | 141.3 |
| AVERAGE OPTICAL TEST DATA | | | | | | | |
| (ISO) Brightness (%) | 83.63 | 83.93 | 83.83 | 84.16 | 84.21 | 84.38 | 84.33 |
| (ISO) Opacity (%) | 77.28 | 78.66 | 78.60 | 78.32 | 78.26 | 76.13 | 77.27 |
| Scattering Coefficient (m^2/kg) | 35.54 | 37.30 | 37.74 | 39.59 | 39.37 | 35.35 | 37.11 |
| Absorption Coefficient (m^2/kg) | 0.28 | 0.29 | 0.29 | 0.29 | 0.29 | 0.26 | 0.27 |
| L* (%) | 95.27 | 95.31 | 95.30 | 95.45 | 95.41 | 95.45 | 95.43 |
| a* (%) | −0.16 | −0.18 | −0.18 | −0.18 | −0.16 | −0.18 | −0.21 |
| b* (%) | 3.56 | 3.41 | 3.36 | 3.37 | 3.24 | 3.16 | 3.16 |

The above specification, examples and data provide a complete description of the manufacture and use of the composition of the invention. Since many embodiments of the invention can be made without departing from the spirit and scope of the invention, the invention resides in the claims hereinafter appended.

We claim:

1. A process for the production of a fiber having a permanently modified fiber morphology, the process comprising:

(a) subjecting a low yield papermaking fiber having a yield of about 55 percent or less to mechanical deformation without substantial fiber breakage resulting in a curled fiber having a temporary curl index of at least 0.15;

(b) subjecting the curled fiber to a treatment with steam at super atmospheric temperature and pressure for a sufficient period of time to render the fiber curl permanent; and (c) explosively releasing the super atmospheric steam, thereby further increasing the curl of the fiber;

wherein the fiber resulting from this process has a permanent curl index of at least 0.20.

2. The process of claim 1 wherein the fiber comprises a purified papermaking wood fiber or recycled papermaking wood fiber.

3. The process of claim 1 wherein the mechanical deformation comprises a hammermill process sufficient to deform the fibers without substantial fiber breakage resulting in a fiber with a curvilinear structure.

4. The process of claim 1 wherein the super atmospheric temperature comprises a temperature of about 130° to 250° C.

5. The process of claim 1 wherein the super atmospheric pressure comprises a pressure of about 40 psi to 405 psi.

6. The process of claim 1 wherein the sufficient period of time comprises a time interval of about 0.1 minute to 30 minutes.

7. The process of claim 1 wherein the fiber resulting from this process has a permanent curl index of about 0.2 to 0.35.

8. The process of claim 1 wherein the fiber resulting from this process has a permanent curl index of about 0.22 to 0.33.

9. The process of claim 1 wherein the fiber with a permanent fiber morphology is blended with a purified papermaking wood fiber at a ratio of about 1 part of the papermaking wood fiber per each 0.01 to 100 parts of the fiber with the permanent fiber morphology.

10. A process for the production of a fiber having a permanently modified fiber morphology, the process comprising:

(a) subjecting a low yield papermaking fiber having a yield of about 55 percent or less to hammermilling without substantial fiber breakage resulting in a curled fiber having a temporary curl index of 0.15 or greater;

(b) subjecting the curled fiber to a treatment with steam at super atmospheric temperature and pressure for about 0.5 minutes to about 20 minutes; and (c) explosively releasing the super atmospheric steam, thereby further increasing the curl index of the fiber;

wherein the fiber resulting from this process has a permanent curl index of from about 0.22 to about 0.33.

11. The process of claim 10 wherein the fiber comprises a purified papermaking wood fiber.

12. The process of claim 10 wherein the super atmospheric temperature comprises a temperature of about 150° to 220° C. within a sealed continuous process container.

13. The process of claim 10 wherein the super atmospheric pressure comprises a pressure of about 40 psi to 230 psi within a sealed continuous process container.

14. The process of claim 10 wherein the subjecting the fiber with the curvilinear structure to a treatment with steam at super atmospheric temperature and pressure occurs for about 1 minute to about 10 minutes within a sealed continuous process container.

15. The process of claim 10 wherein the fiber with a permanent fiber morphology is blended with a purified papermaking wood fiber at a ratio of about 1 part of the papermaking wood fiber per each 1 to 100 parts of the fiber with the permanent fiber morphology.

16. A process for the production of a fiber having a permanently modified fiber morphology, the process comprising:

(a) subjecting a low yield papermaking fiber having a yield of about 55 percent or less to mechanical deformation without substantial fiber breakage resulting in a curled fiber having a temporary curl index of about 0.15 or greater;

(b) subjecting the curled fiber to a treatment with steam at super atmospheric temperature and pressure for a sufficient period of time to render the fiber curl permanent; and (c) explosively releasing the super atmospheric steam, thereby further increasing the curl of the fiber about 100 percent, wherein the fiber resulting from this process has a permanent curl index of from about 0.3 to about 0.4.

* * * * *